(12) United States Patent
Hossack et al.

(10) Patent No.: US 6,179,780 B1
(45) Date of Patent: Jan. 30, 2001

(54) METHOD AND APPARATUS FOR MEDICAL DIAGNOSTIC ULTRASOUND REAL-TIME 3-D TRANSMITTING AND IMAGING

(75) Inventors: John A. Hossack, Palo Alto; Thilaka S. Sumanaweera, San Jose, both of CA (US)

(73) Assignee: Acuson Corporation, Mountain View, CA (US)

( * ) Notice: Under 35 U.S.C. 154(b), the term of this patent shall be extended for 0 days.

(21) Appl. No.: 09/370,059

(22) Filed: Aug. 6, 1999

(51) Int. Cl.[7] ........................................... A61B 8/00
(52) U.S. Cl. ................................................. 600/437
(58) Field of Search ................... 600/443, 444, 600/437, 438, 459, 447; 128/916; 367/11, 7

(56) References Cited

U.S. PATENT DOCUMENTS

| | | | | |
|---|---|---|---|---|
| 4,456,982 | * | 6/1984 | Tournois | 367/11 |
| 4,694,434 | * | 9/1987 | von Ramm et al. | 367/7 |
| 4,798,210 | * | 1/1989 | Ledley | 600/438 |
| 5,027,820 | * | 7/1991 | Pesque | 600/443 |
| 5,105,814 | * | 4/1992 | Drukarey et al. | 600/443 |
| 5,623,928 | * | 4/1997 | Wright et al. | 600/443 |
| 5,675,554 | | 10/1997 | Cole et al. . | |
| 5,735,282 | * | 4/1998 | Hossack | 600/459 |
| 5,808,962 | | 9/1998 | Steinberg et al. . | |

OTHER PUBLICATIONS

Matthew O'Donnell, Coded Excitation System for Improving the Penetration of Real–Time Phased–Array Imaging Systems, IEEE Transactions on Ultrasonics, Ferroelectrics, and Frequency Control, vol. 39, No. 3, May 1992, pp. 341–351.

Multidimensional Ultrasonic Imaging for Cardiology, Hugh A. McCann et al., Proceedings of the IEEE, vol. 76, No. 9, Sep. 1988, pp. 1063–1076.

* cited by examiner

Primary Examiner—Marvin M. Lateef
Assistant Examiner—Maulin Patel
(74) Attorney, Agent, or Firm—Brinks Hofer Gilson & Lione

(57) ABSTRACT

A medical diagnostic ultrasound real-time 3-D transmitting and imaging system generates multiple transmit beam sets using a 2-D transducer array. Each transmit beam set includes multiple simultaneous ultrasound transmit beams. The system acquires multiple receive beam sets in response to the transmit beams, and each receive beam set includes multiple simultaneous receive beams. A real-time, three-dimensional medical diagnostic ultrasound image is formed in response to these receive beams. Several techniques for reducing cross talk in such a system are discussed.

26 Claims, 4 Drawing Sheets

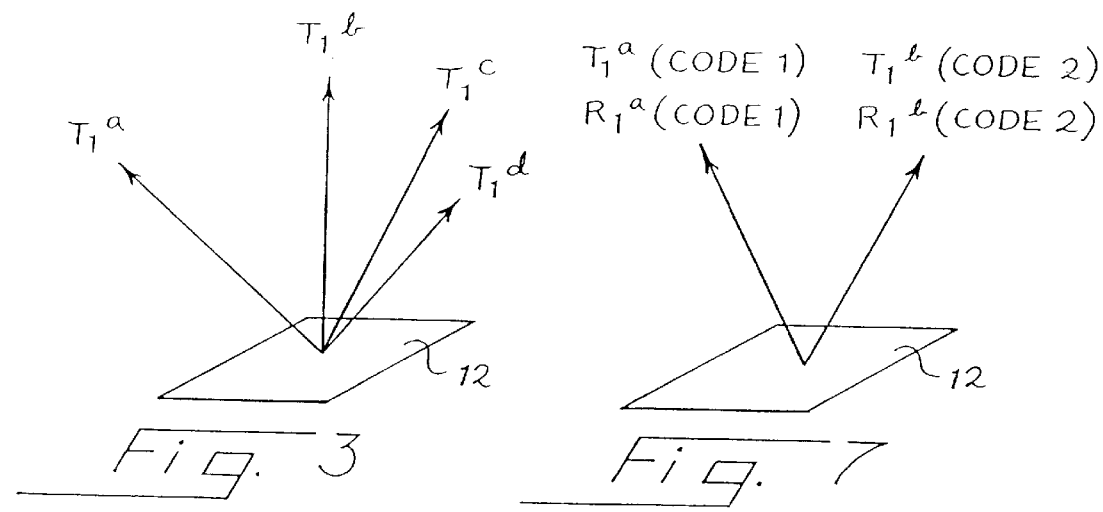
Fig. 3
Fig. 7
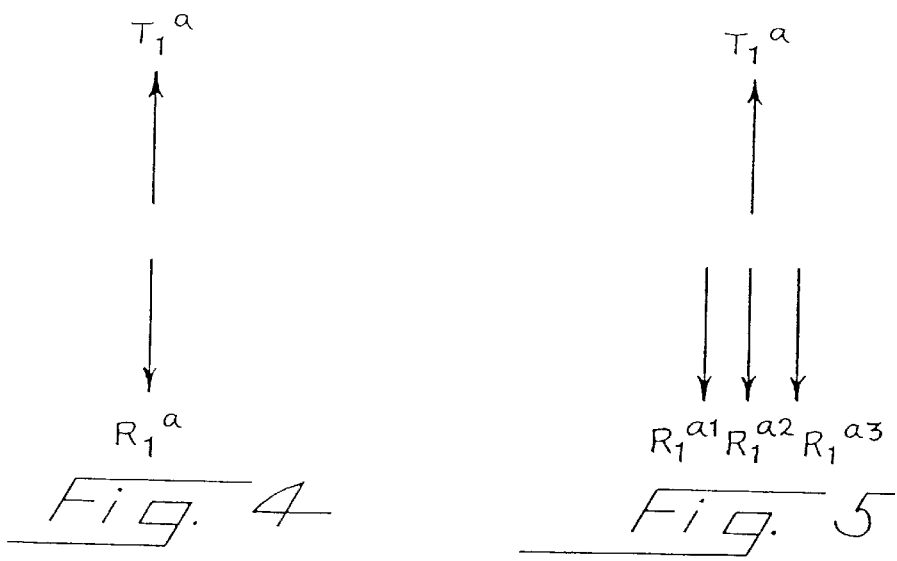
Fig. 4
Fig. 5
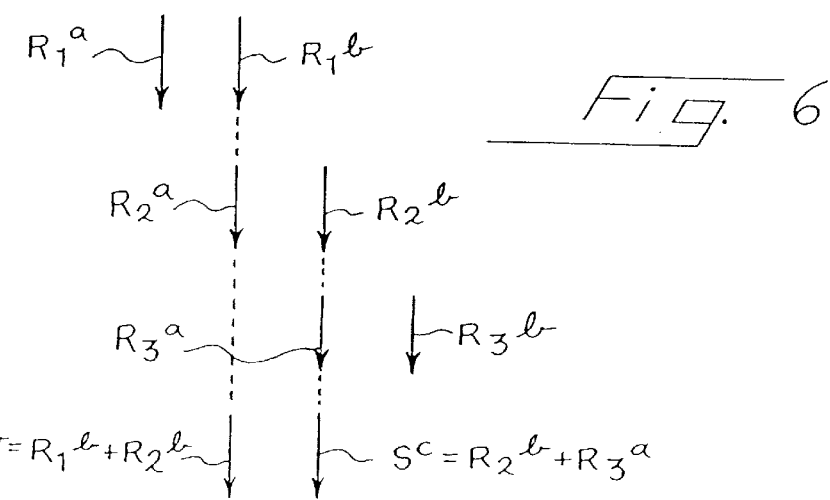
Fig. 6

METHOD AND APPARATUS FOR MEDICAL DIAGNOSTIC ULTRASOUND REAL-TIME 3-D TRANSMITTING AND IMAGING

BACKGROUND

This invention relates to medical diagnostic ultrasound imaging, and in particular to the real-time acquisition of 3-D ultrasound images.

Real-time 3-D ultrasound image acquisition relies on two-dimensional (2-D) transducer arrays to acquire ultrasound image data over a 3-D imaged volume in real-time.

The two-way transmit time for the acoustic pulse is the fundamental frame rate limiting parameter in ultrasound imaging. The problem of low frame rate becomes severe in three-dimensional real-time imaging. If the maximum imaging depth is 150 millimeters and the application requires 20 frames per second, then there are a maximum of about 256 transmit events per frame. The standard response to this problem is to use multiple receive lines per transmit event to achieve a higher spatial sampling rate.

One prior-art system marketed by Volumetrics uses a 16×16 transmit line firing pattern. A 4×4 receive line reception pattern is acquired for each transmit firing. This results in coarse sampling that has an adverse impact on image quality and that fundamentally limits resolution. The Volumetrics system currently operates with a 65° pyramid, rather than the 90° pyramid which is often preferred. The reduced field of view is at least partially used in order to improve frame rate, but a 65° pyramid is inherently limited in terms of clinical utility. When looking at a 2-D slice through the acquired 3-D volume, the approach taken by the Volumetrics system is equivalent to having used only 16 transmit beams and 16×4 (64) receive beams for each 2-D slice.

SUMMARY

Thus, a need presently exists for an improved ultrasound 3-D transmitting method that improves frame rate and/or spatial resolution as compared to the prior art approach described above. By way of introduction, the preferred embodiments described below generate multiple transmit beam sets with a 2-D transducer array, and each transmit beam set comprises multiple simultaneous ultrasound transmit beams. By increasing the number of transmit beams per transmit event, the frame rate and/or the spatial resolution of the resulting three-dimensional real-time image is increased. The present invention is defined by the following claims, and nothing in this section should be taken as a limitation on those claims.

BRIEF DESCRIPTION OF THE DRAWINGS

FIG. 3 is a schematic diagram showing four simultaneous transmit beams within a single transmit event.

FIGS. 4 and 5 are schematic representations of two alternative receive beam patterns associated with a single transmit beam.

FIG. 6 is a schematic representation of a method for forming synthetic receive beams.

FIG. 7 is a schematic representation of a method that uses coded transmit beams and decoded receive beams.

BRIEF DESCRIPTION OF THE PREFERRED EMBODIMENTS

Figure 1:
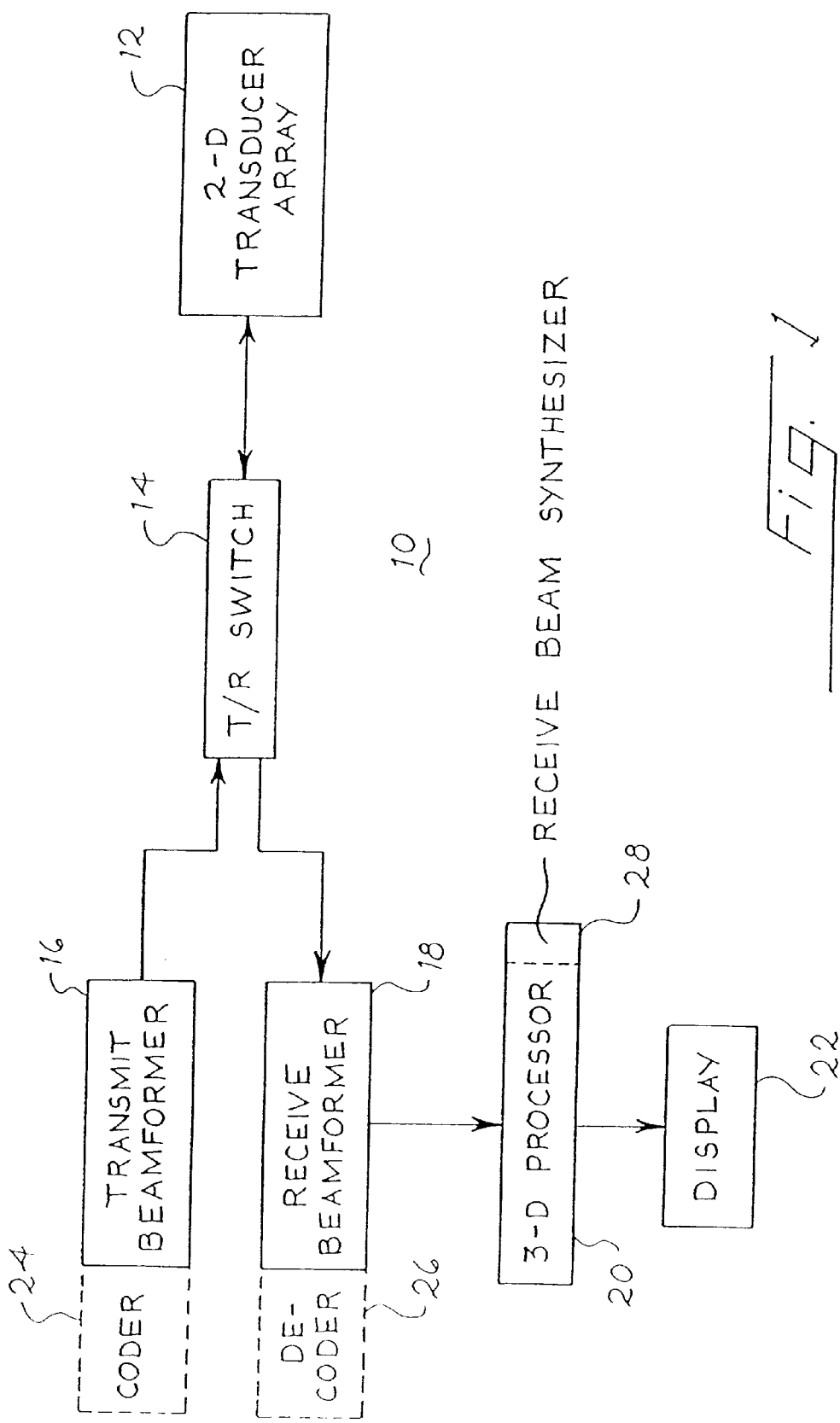
FIG. 1 is a block diagram of a medical diagnostic ultrasound imaging system that incorporates a preferred embodiment of this invention.

Turning now to the drawings, FIG. 1 shows an ultrasound imaging system 10 that includes a 2-D transducer array 12 that is coupled via a transmit/receive switch 14 to a transmit beamformer 16 and a receive beamformer 18. The beamformer 16 includes an optional coder 24, and the beamformer 18 includes an optional decoder 26 as described below. Receive beams acquired by the receive beamformer 18 are applied to a 3-D processor 20 that optionally includes a receive beam synthesizer 28. The receive beam processor 20 generates a three-dimensional dataset that is used to form images from desired viewpoints and for desired views on a display 22.

Except for the differences outlined below, the elements 12 through 22 can be substantially conventional. For example, any suitable 2-D transducer array 12 can be used, including 2-D arrays arranged on either a planar or a non-planar surface. 2-D sparse arrays with randomly distributed elements and arrays with elements distributed on a spiral (see, e.g., U.S. Pat. No. 5,808,962) can also be used. The transmit beamformer is preferably constructed according to the principles described in Cole U.S. Pat. No. 5,675,554 to form multiple spaced transmit beams within each transmit event. Multiple spaced transmit beams are discussed in the context of 2-D imaging in the Cole patent, without any specific suggestion that such multiple simultaneous transmit beams should be used with a 2-D array. The present invention is not limited to use with transmit beamformers of this type. Alternate beamformer architectures, including architectures with a frequency dependent focus as described in Hossack U.S. Pat. No. 5,608,690 or beamformers such as that used in the Volumetrics system described above, can also be used.

Figure 2:
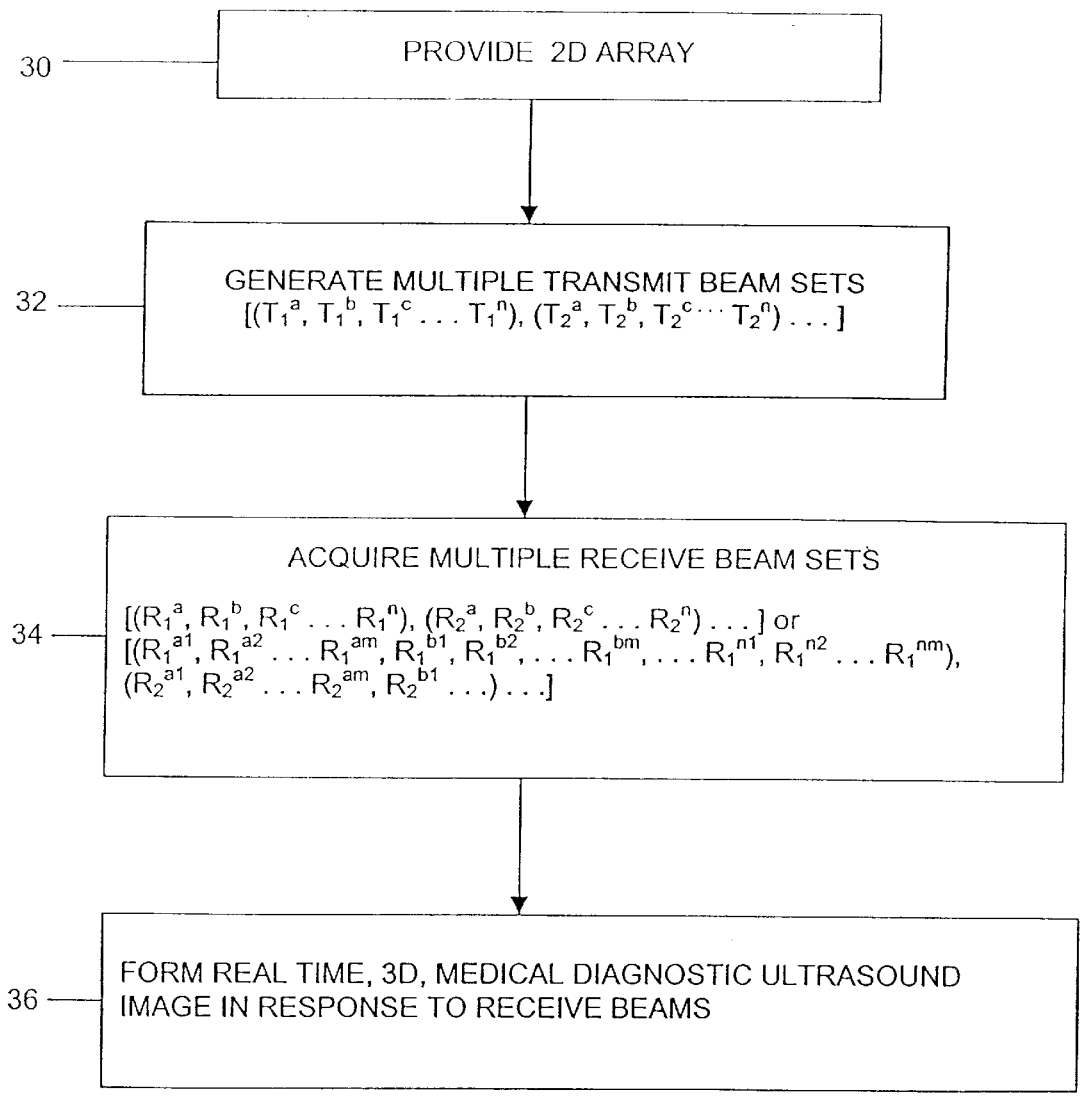
FIG. 2 is a block diagram of a method implemented by the system of FIG. 1.

FIG. 2 flowcharts a method performed by the system of FIG. 1. A two-dimensional array 12 is provided at 30. The transmit beamformer 16 generates multiple transmit beam sets at 32, each set including multiple simultaneous transmit beams. In this specification transmit beams are indicated by the symbol T, receive beams are indicated by R, subscripts indicate the beam set, and superscripts indicate the beam number within the beam set. Thus, transmit beam $T_1^a$ is the transmit beam a of the first beam set. Typically, $T_1^a$ will be directed along a different direction than $T_2^a$, and the superscripts are intended only to signify the relative order of the transmit beams within the set, not the absolute spatial direction of the transmit beams. Taken as a whole, the transmit beam sets of block 32 are spatially distributed to scan the region of interest in both elevation and azimuth. FIG. 3 provides one schematic illustration of a transmit beam set that includes four simultaneous transmit beams $T_1^a$, $T_1^b$, $T_1^c$ and $T_1^d$. As shown in FIG. 3, all four transmit beams of the illustrated transmit beam set are directed in separate respective directions.

Returning to FIG. 2, multiple receive beam sets are acquired at 34 in response to the transmit beam sets. In the simplest embodiment, a single receive beam is acquired in response to each of the transmit beams, along the same direction as the respective transmit beam. This approach is illustrated in FIG. 4, where the transmit beam $R_1^a$, is acquired from and spatially aligned with the transmit beam $T_1^a$. In this embodiment only a single receive beam is acquired for each transmit beam.

In more preferred embodiments, multiple receive beams are acquired from each transmit beam. This approach is illustrated by way of a simple example in FIG. 5, where three spatially distinct receive beams $R_1^{a1}$, $R_1^{a2}$, $R_1^{a3}$, are all acquired simultaneously from a single respective transmit beam $T_1^a$. In the general case M receive beams are acquired from each of the transmit beams of each of the transmit beam sets. For example, M can equal 4, 8, 16 or some other number.

Returning to FIG. 2, a real-time, three-dimensional, medical diagnostic ultrasound image is formed at 36 by the 3-D processor 20 of FIG. 1 in response to the receive beams described above. The ultrasound image is then displayed on the display 22.

When two beams are simultaneously transmitted there is a danger of cross talk. This is because receive beamforming must play a greater role than usual to separate the separate transmit beams. The performance of receive beamforming in the presence of typical levels of tissue-related phase aberration is measurably degraded from theoretical ideal performance levels, making the cross-talk issue more significant. Various methods can be used for improving beam separation, including those described below.

Synthetic Receive Beams

One approach is to provide the 3-D processor 20 with a receive beam synthesizer 28, as shown in FIG. 1. The receive beam synthesizer 28 uses techniques similar to those described in Wright U.S. Pat. No. 5,6623,928, assigned to the assignee of the present invention, to synthesize additional receive beams from two or more of the acquired receive beams generated by the receive beamformer 18. For example, the receive beam synthesizer 28 can implement the method illustrated in FIG. 6. In this method, only a few of the many receive beams are shown for clarity of illustration. First, two receive beams $R_1^a$ and $R_1^1$ are acquired. Next, additional receive beams are $R_2^a$ and $R_2^b$ are acquired. Note that $R_1^b$ is spatially aligned with $R_2^a$. Next, two further receive beams $R_3^a$ and $R_3^b$ are acquired. In this case $R_3^a$ is spatially aligned with $R_2^b$. Synthetic receive beam $S^b$ is formed by summing $R_1^b$ and $R_2^a$. Note that this synthetic beam $S^b$ and the acquired receive beams $R_1^b$, $R_2^a$ are all collinear. Similarly, the synthetic receive beam $S^c$ is formed by summing the receive beams $R_2^b$ and $R_3^a$. In synthetic beams $S^b$, $S^c$, the desired signal is doubled since it adds constructively. Simultaneously-acquired responses to adjacent transmit beams do not add constructively and are effectively reduced with respect to the desired signal that is spatially aligned with the synthetic receive beam.

Coded Transmissions

Another approach for reducing cross talk is to use coded transmissions. For example, a separate pseudo-random binary sequence can be used to code each transmit beam within a set. Ideally, the transmission codes are selected so that the response of two simultaneous firings are close to orthogonal (non-interfering). Coded echoes are decoded with the respective transmission code during the receive beamforming operation to recover an impulse-like response. Suitable decoding techniques include correlation techniques and matched filters. Such techniques are described in detail in copending U.S. patent application Ser. No. 09/283,346, filed Mar. 31, 1999, and assigned to the assignee of the present invention. Preferably, the code rate of the transmission codes is chosen such that the bandwidth of the convolved code is compatible with the bandwidth of the transducer. Preferably, transmission amplitudes are used which minimize the effect of non-linear propagation which may interfere with the coding/decoding operation. Alternatively, one can estimate the impact of non-linear propagation on the coded pulse and use the modified estimated pulse for the decorrelation operation.

As shown in FIG. 1, the transmit beamformer 16 can include a coder 24 and the receive beamformer 18 can include a decoder 26. Preferably, there is at least one decoder 26 for each code being used. Alternatively, the received signals are buffered and sequentially decoded. Any suitable coded waveform can be used. As used herein, the term "transmission code" refers to a multipulse transmission with non-uniform interpulse spacing. Two examples of transmission codes include chirp pulses with a rising chirp and chirp pulses with a falling chirp. FIG. 7 shows one example of two simultaneous transmit beams $T_1^a$ (Code 1) and $T_1^b$ (Code 2). Each of the two transmit beams of FIG. 7 is coded with a separate respective transmission code. The corresponding receive beams $R_1^a$ (Code 1) and $R_1^b$ (Code 2) are decoded with the respective transmission codes used for the corresponding transmit beams. By using coded transmissions, the ability to discriminate among reflections from multiple simultaneous transmit pulses is increased, and the signal to noise ratio is improved due to the increased energy that is transmitted for a given peak power level.

Various coded transmission techniques are known to the art, using a shaped pulse transmitter such as that disclosed in U.S. Pat. No. 5,675,554. See, for example M. O'Donnell, "Coded Excitation System for Improving the Penetration of Real Time Phased Array Imaging Systems," IEEE Trans. UFFC Vol. 39, No. 3, pp. 341–351 (May, 1992). Pseudo-random code sequences such as Barker and Golay codes can also be used. Golay codes are preferably used in pairs such that their side lobes are opposite in phase and cancel on addition of the complementary decoded signals.

Receive Beam Null Placement

Figure 8:
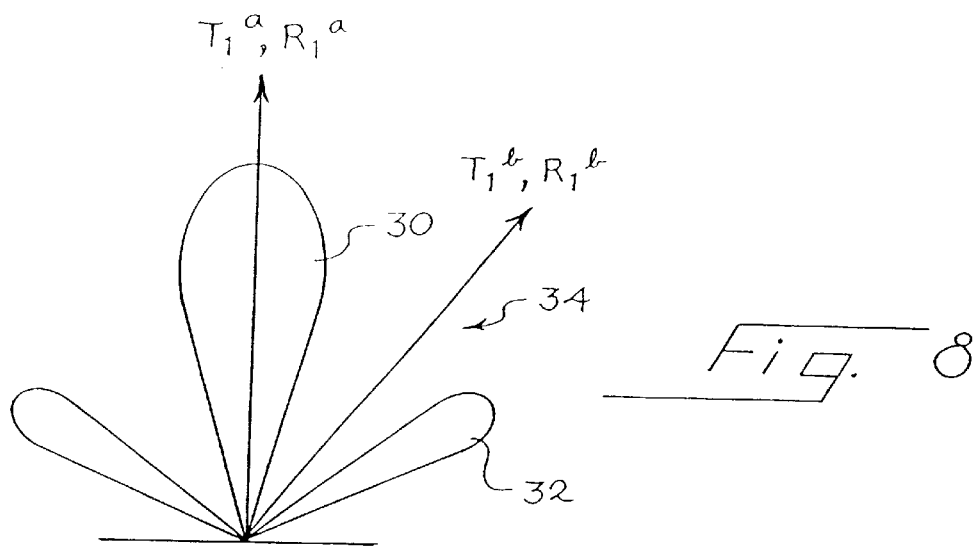
FIG. 8 is a diagram showing one transmit beam positioned in a null of another receive beam.

Another alternative for reducing cross talk is illustrated schematically in FIG. 8. In FIG. 8 the sensitivity of a receive beam $R_1^a$ is shown as including a main lobe 30 and two side lobes 32. A null 34 exists between the main lobe 30 and the side lobe 32. In this case a transmit beam $T_1^b$ and an associated receive beam $R_1^b$ are positioned in the null 34. In this way, the sensitivity of the receive beam $R_1^a$ to echoes from the transmit beam $T_1^b$ is reduced. If necessary, the apodization profile can be deliberately shaped to create such nulls.

Non-Uniform Scanning Sequences

Figure 9:
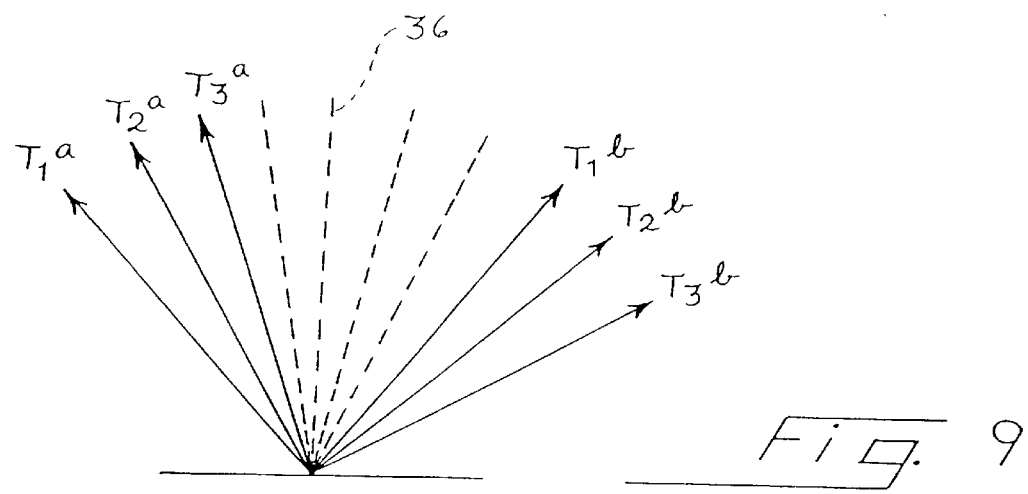
FIG. 9 is a schematic diagram showing a transmit beam scanning sequence.

FIG. 9 illustrates another method for reducing cross talk. As shown in FIG. 9, two simultaneous transmit beams $T_1^a$, $T_1^b$ are widely separated by a number of intervening transmit lines 36. In this way, the impact of any shadow beamformed reflected data from a non-desired transmit beam is broken up and does not appear continuous in the resultant image.

Different Transmit Center Frequencies

Figure 10:
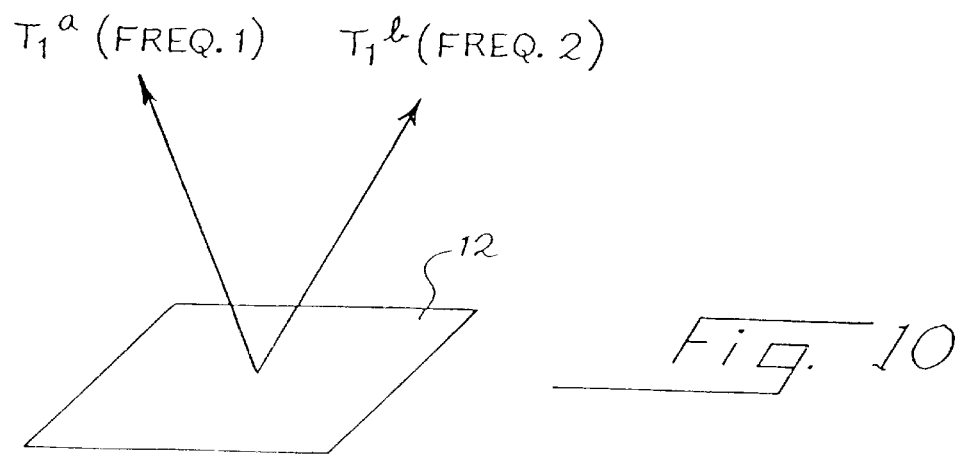
FIG. 10 is a schematic diagram showing transmit beams using different transmit center frequencies.

FIG. 10 shows another approach that can be used to reduce cross talk. In this approach the transmit beams within a transmit beam set are modulated with separate respective transmit center frequencies. In FIG. 10, the transmit beam $T_1^a$ is modulated with a first transmit center frequency FREQ1 and transmit beam $T_1^b$ is modulated with a second transmit center frequency FREQ2. The receive beamformer includes filtering that allows separation of the echoes from the respective transmit beams.

Concluding Statements

It should be apparent that the preferred embodiments described above can be used substantially to improve the frame rate or the spatial resolution of 3-D real-time ultrasound images. Because the disclosed method uses focused transmit beams, tissue harmonic images can be generated if desired.

The preferred embodiments described above can be used in any suitable ultrasound imaging mode, including for example tissue harmonic imaging, contrast harmonic imaging, B-mode imaging, color Doppler imaging, spectral Doppler imaging, and frequency dependent focus imaging.

The 2-D array 12 can be a fully populated array or a sparse array. The number of elements and the dimensions of elements may be the same in the azimuthal and elevation directions or different in the azimuthal and elevation directions.

As used herein the term "set" is used to indicate two or more.

The term "real-time" means that the three-dimensional image is displayed to a user during an ultrasound imaging session in which the images are obtained shortly after the image information was acquired.

The term "simultaneous transmit beams" refers to transmit beams that are part of the same transmit event and that are in flight in overlapping time periods. Simultaneous transmit beams do not have to begin precisely at the same instant or to terminate precisely at the same instant. Similarly, simultaneous receive beams are receive beams that are acquired from the same transmit event, whether or not they start or stop at precisely the same instant.

The term "additional receive beam" refers to synthesized receive beams that may be spatially aligned with the corresponding acquired receive beams or spatially separated from the corresponding acquired receive beams.

The term "transmit lines" refers to spatial directions on which transmit beams are positioned at some time during an imaging operation.

The term "3-D image" is intended broadly to encompass any image formed from a 3-D data set, including sectional views and various types of renderings and projections, for example.

The foregoing detailed description has discussed only a few of the many forms that this invention can take. For this reason, this detailed description is intended only by way of illustration and not by way of limitation. It is only the following claims, including all equivalents, that are intended to define the scope of this invention.

What is claimed is:

1. A medical, diagnostic, ultrasound, real-time, 3-D transmitting method comprising:
   (a) providing a 2-D transducer array and a transmit beamformer coupled with the 2-D transducer array; and
   (b) generating multiple transmit beam sets with the 2-D transducer array and the transmit beamformer, each transmit beam set comprising multiple simultaneous transmit beams.

2. The method of claim 1 further comprising:
   (c) acquiring multiple receive beam sets in response to the transmit beams generated in (b), each receive beam set comprising multiple simultaneous receive beams.

3. The method of claim 2 further comprising:
   (d) forming a real-time, 3-D medical diagnostic ultrasound image in response to the receive beams acquired in (c).

4. The method of claim 2 wherein (c) comprises synthesizing additional receive beams in response to the acquired receive beams of (c).

5. The method of claim 3 wherein (c) comprises synthesizing additional receive beams spatially aligned with respective ones of the acquired receive beams of (c).

6. The method of claim 1 wherein (b) comprises:
   (b1) coding at least two of the simultaneous transmit beams in each transmit beam set with separate respective transmission codes.

7. The method of claim 2 wherein (b) comprises:
   (b1) coding at least two of the simultaneous transmit beams in each transmit beam set with separate respective transmission codes; and
   wherein (c) comprises
   (c1) decoding at least two of the simultaneous receive beams.

8. The method of claim 6 wherein at least two of the transmission codes are substantially non-interfering with one another.

9. The invention of claim 2 wherein one of the simultaneous receive beams comprises a null, and wherein at least one of the transmit beams is aligned with the null.

10. The invention of claim 3 wherein one of the simultaneous receive beams comprises a null, and wherein at least one of the receive beams is aligned with the null.

11. The method of claim 1 wherein the transmit beams in each transmit beam set are separated by a plurality of transmit lines.

12. The method of claim 1 wherein (b) comprises:
   (b) generating at least two of the transmit beams of each transmit beam set with separate respective transmit center frequencies.

13. The method of claim 1 wherein the multiple simultaneous transmit beams of at least a first one of the transmit beam sets are directed in (b) in separate respective directions distributed in three spatial dimensions.

14. A medical, diagnostic, ultrasound, real-time, 3-D transmitting system comprising:
   a 2-D transducer array; and
   a transmit beamformer coupled with the 2-D transducer array and operative to generate multiple transmit beam sets with the array, each transmit beam set comprising multiple simultaneous transmit beams.

15. The invention of claim 14 in combination with:
   a receive beamformer coupled with the 2-D transducer array and operative to acquire multiple receive beam sets in response to the transmit beams, each receive beam set comprising multiple simultaneous receive beams.

16. The invention of claim 14 in combination with:
   a 3-D processor coupled with the receive beamformer and operative to form a real-time, 3-D, medical diagnostic ultrasound image in response to the receive beams.

17. The invention of claim 15 wherein the 3-D processor comprises means for synthesizing additional receive beams in response to the receive beams acquired by the receive beamformer.

18. The invention of claim 16 wherein the 3-D processor comprises means for synthesizing additional receive beams spatially aligned with respective ones of the receive beams acquired by the receive beamformer.

19. The invention of claim 14 wherein the transmit beamformer comprises means for coding at least two of the simultaneous transmit beams in each transmit beam set with separate respective transmission codes.

20. The invention of claim 15 wherein the transmit beamformer comprises means for coding at least two of the simultaneous transmit beams in each transmit beam set with separate respective transmission codes, and wherein the receive beamformer comprises means for decoding two of the simultaneous receive beams.

21. The invention of claim 19 wherein at least two of the transmission codes are substantially non-interfering with one another.

22. The invention of claim 15 wherein one of the simultaneous receive beams comprises a null, and wherein at least one of the transmit beams is aligned with the null.

23. The invention of claim 15 wherein one of the simultaneous receive beams comprises a null, and wherein at least one of the receive beams is aligned with the null.

24. The invention of claim 14 wherein the transmit beams in each transmit beam set are separated by a plurality of transmit lines.

25. The invention of claim 14 wherein the transmit beamformer generates at least two of the transmit beams of each transmit beam set with separate respective transmit center frequencies.

26. The invention of claim 14 wherein the multiple simultaneous transmit beams of at least a first one of the transmit beam sets are directed in separate respective directions distributed in three spatial dimensions.

* * * * *

UNITED STATES PATENT AND TRADEMARK OFFICE
CERTIFICATE OF CORRECTION

PATENT NO. : 6,179,780 B1
DATED : January 30, 2001
INVENTOR(S) : John A. Hossack et al.

It is certified that error appears in the above-identified patent and that said Letters Patent is hereby corrected as shown below:

Column 6,
Line 49, delete "claim 14" and substitute -- claim 15 -- in its place.

Signed and Sealed this

Fifth Day of November, 2002

Attest:

Attesting Officer

JAMES E. ROGAN
Director of the United States Patent and Trademark Office